(12) United States Patent
Lin et al.

(10) Patent No.: US 10,526,333 B2
(45) Date of Patent: Jan. 7, 2020

(54) RUTAECARPINE ANALOGS AND APPLICATIONS THEREOF

(71) Applicants: TAIPEI MEDICAL UNIVERSITY, Taipei (TW); NATIONAL TAIPEI UNIVERSITY OF TECHNOLOGY, Taipei (TW)

(72) Inventors: Chun-Mao Lin, Taipei (TW); Chi-Ming Lee, Taipei (TW); Chi Wang, Taipei (TW); Sheng-Tung Huang, Taipei (TW); Jiun-An Gu, Taipei (TW); Tin-An Rau, Taipei (TW)

(73) Assignees: TAIPEI MEDICAL UNIVERSITY, Taipei (TW); NATIONAL TAIPEI UNIVERSITY OF TECHNOLOGY, Taipei (TW)

( * ) Notice: Subject to any disclaimer, the term of this patent is extended or adjusted under 35 U.S.C. 154(b) by 0 days.

(21) Appl. No.: 15/952,644

(22) Filed: Apr. 13, 2018

(65) Prior Publication Data
US 2019/0315746 A1    Oct. 17, 2019

(51) Int. Cl.
*C07D 471/14* (2006.01)
*A61K 31/519* (2006.01)
*A61P 29/00* (2006.01)

(52) U.S. Cl.
CPC ............ *C07D 471/14* (2013.01); *A61P 29/00* (2018.01)

(58) Field of Classification Search
CPC .............................. C07D 471/14; A61P 29/00
See application file for complete search history.

(56) References Cited

PUBLICATIONS

Lee et al., Synthetic fluororutaecarpine inhibits inflammatory stimuli and activates endothelial transient receptor potential vanilloid-type 1, Molecules (2017), 22(4), 656/1-656/12.*
Lee, Chi-Ming, et al., "Synthetic Fluororutaecarpine Inhibits Inflammatory Stimuli and Activates Endothelial Transient Receptor Potential Vanilloid—Type 1," Molecules 2017, 22, 656.
Lee, Chi-Ming, et al., "Low-Cytotoxic Synthetic Bromorutaecarpine Exhibits Anti-Inflammation and Activation of Transient Receptor Potential Vanilloid Type 1 Activities," Hindawi Publishing Corporation, BioMed Research International, vol. 2013, Article ID 795095.

\* cited by examiner

*Primary Examiner* — Alexander R Pagano
*Assistant Examiner* — Ebenezer O Sackey
(74) *Attorney, Agent, or Firm* — Duane Morris LLP

(57) ABSTRACT

The present invention provides RUT analogs with various biological activities. In particular, the biological activities comprise anti-inflammatory activity, vasodilator effects, migration/invasion-suppressive activities, ability against damage due to remodeling between the epithelium and endothelium, collagen deposition and cardiac fibrosis suppress, Snail protein inhibitory effect, etc., which may improve cardiac, vasodilation, and lung functions. The RUT analogs disclosed herein also exhibit a lower cytotoxicity comparing to RUT.

12 Claims, 11 Drawing Sheets

RUTAECARPINE ANALOGS AND APPLICATIONS THEREOF

FIELD OF THE INVENTION

The present invention relates to rutaecarpine analogs, in particular fluorinated rutaecarpine. The present invention also relates to medical applications of rutaecarpine analogs.

BACKGROUND OF THE INVENTION

Endothelial cells (ECs) of arteries are important for the trafficking of nutrients and participate in many physiologic events, such as inflammation and angiogenesis. Atherosclerosis is primarily associated with a series of reactions within the tunica intima and involves monocyte recruitment, macrophage formation, lipid accumulation, extracellular matrix (ECM) production, and smooth muscle cell migration. Compounds with inhibitory effects on vascular inflammation and cell migration would be beneficial for antiatherogenic progression.

Rutaecarpine (RUT) is one of the main bioactive ingredients extracted from the traditional medicine Evodia rutaecarpa and can improve atherosclerosis by preventing monocyte adhesion to the vascular endothelium. RUT reduced the prostaglandin production of lipopolysaccharide (LPS)-activated RAW264.7 macrophages, but did not affect levels of cyclooxygenase (COX)-2 messenger (m)RNA or protein. The vasorelaxant effect of RUT in isolated mesenteric arteries was reported to be associated with $Ca^{2+}$ flux activity based on in vivo tests on mice. RUT lowered blood pressure through the endothelial $Ca^{2+}$-nitric oxide (NO)-cGMP pathway to reduce residual muscle tension. The calcitonin gene-related peptide (CGRP), a major neurotransmitter produced in peripheral and central neurons, plays a key role in maintaining endothelial homoeostasis. Decreased plasma CGRP levels cause cardiac susceptibility to ischemia-reperfusion injury, and RUT reverses that decrease by stimulating CGRP production. CGRP counteracts angiotensin (Ang) II-induced endothelial progenitor cell senescence by suppressing reactive oxygen species (ROS) and NADPH oxidase.

Activation of transient receptor potential vanilloid type 1 (TRPV1) in ECs may protect against cardiovascular diseases such as hypertension and stroke. Release of CGRP by activation of vanilloid receptors plays an important role in the vasodilation effects of RUT. NO released by activation of endothelial NO synthase (eNOS) leads to vascular relaxation mediated by CGRP and TRPV1 stimulation. TRPV1-dependent atheroprotection was demonstrated in mice. RUT was reported to be a potential therapeutic agent for arterial thrombosis because of its antiplatelet effect in vivo. Alkaloid compounds also showed anticancer activities by inducing cell cycle arrest or apoptosis in vitro and in vivo. RUT showed high toxicity to lymphoblasts and inhibited ATP-dependent efflux pumps in a blood-brain barrier model with porcine brain capillary ECs, that thus restricts its application in vascular diseases. A variety of structural modifications of natural products were designed and synthesized for better biological applications. RUT derivatives were designed and synthesized to activate TRPV1 for enhanced vasodilator and hypotensive effects. The 14-N atom of RUT is critical for its activity. Bromo-rutaecarpine was designed to broaden the potential for application. However, the bromo-derivative may not be stable enough due to it being more bulky in substitution.

There are still needs for RUT analogs which exhibit very low cytotoxicity, but maintain the anti-inflammatory activity and TRPV1-upregulating effects.

SUMMARY OF THE INVENTION

The present invention provides RUT analogs with various biological activities. In particular, the biological activities comprise anti-inflammatory activity, vasodilator effects, migration/invasion-suppressive activities, ability against damage due to remodeling between the epithelium and endothelium, collagen deposition and cardiac fibrosis suppress, Snail protein inhibitory effect, etc., which may improve cardiac, vasodilation, and lung functions. The RUT analogs disclosed herein also exhibit a lower cytotoxicity comparing to RUT.

Accordingly, the present invention provides a compound having the following Formula (I) as described herein.

The present invention also provides a pharmaceutical composition comprising a compound as described herein, or a pharmaceutically acceptable ester, salt, or prodrug thereof, together with a pharmaceutically acceptable carrier.

The present invention also provides a method of ameliorating inflammation in a subject, comprising a step of administering a compound as described herein to the subject.

The present invention also provides a method of suppressing nitrogen oxide (NO) release in a subject, comprising a step of administering as described herein to the subject.

The present invention further provides a method of suppressing TNF-α release and/or inhibiting cell migration, cell invasion or both in a subject, comprising a step of administering a compound as described herein to the subject.

DETAILED DESCRIPTION OF THE INVENTION

Figure 1A:
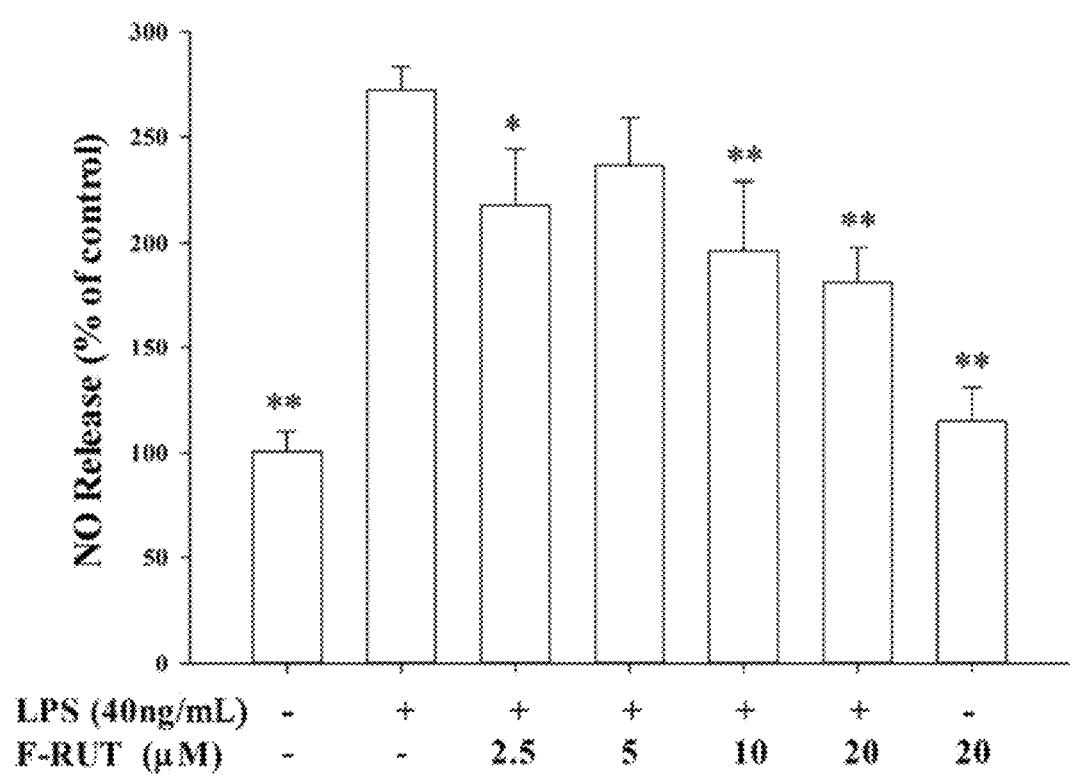
FIG. 1A thru 1C show the effects of 10-fluoro-2-methoxy-rutaecarpine (F-RUT) on nitric oxide (NO) and tumor necrosis factor (TNF)-α release by lipopolysaccharide (LPS)-treated (40 ng/mL) RAW264.7 macrophages: (a) NO levels were detected in culture medium using the Griess reaction; (b) TNF-α release in cell supernatants was detected using a mouse TNF-α Quantikine kit; (c) Cell viability upon F-RUT and rutaecarpine (RUT) treatment for 24 h in an MTT assay. Values are expressed as the mean±SE. *p<0.05, **p<0.01.

Unless otherwise defined, all technical and scientific terms used herein have the same meaning as commonly understood by one of ordinary skill in the art to which this invention belongs applying that term in context to its use in describing the present invention. The terminology used in the description is for describing particular embodiments only and is not intended to be limiting of the invention.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

The terms "halo" and "halogen," as used herein, refer to an atom selected from fluorine, chlorine, bromine and iodine.

The term "alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless specifically stated otherwise in the specification, an alkyl group is optionally substituted by one or more of substituents. The term "alkenyl," as used herein, denotes a monovalent group derived from a hydrocarbon moiety containing, in certain embodiments, from two to six, or two to eight carbon atoms having at least one carbon-carbon double bond. The double bond may or may not be the point of attachment to another group. Alkenyl groups include, but are not limited to, for example, ethenyl, propenyl, butenyl, 1-methyl-2-buten-1-yl, heptenyl, octenyl and the like.

The term "alkoxy" refers to a radical bonded through an oxygen atom of the formula —O-alkyl, where alkyl is an alkyl chain as defined above.

The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, ascorbate, adipate, alginate, aspirate, benzenesulfonate, benzoate, bicarbonate, bisulfate, bitartrate, borate, bromide, butyrate, camphorate, camphorsulfonate, camsylate, carbonate, chloride, clavulanate, citrate, cyclopentane propionate, diethylacetic, digluconate, dihydrochloride, dodecylsulfanate, edetate, edisylate, estolate, esylate, ethanesulfonate, formate, fumarate, gluceptate, glucoheptanoate, gluconate, glutamate, glycerophosphate, glycollylarsanilate, hemisulfate, heptanoate, hexanoate, hexylresorcinate, hydrabamate, bromide, chloride, 2-hydroxyethanesulfonate, hydroxynaphthoate, iodide, isonicotinate, isothionate, lactate, lactobionate, laurate, malate, maleate, mandelate, mesylate, methylnitrate, methylsulfate, methanesulfonate, mucate, 2-naphthalenesulfonate, napsylate, nicotinate, nitrate, oleate, oxalate, pamoate (embonate), palmitate, pantothenate, pectinate, persulfate, phosphate/diphosphate, pimelate, phenylpropanoate, polygalacturonate, propionate, salicylate, stearate, sulfate, subacetate, succinate, tannate, tartrate, teoclate, thiocyanate, tosylate, triethiodide, trifluoroacetate, undeconate, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. Also, included are the basic nitrogen-containing groups that may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

The term "subject" includes living organisms such as humans, monkeys, cows, sheep, horses, pigs, cattle, goats, dogs, cats, mice, rats, cultured cells, and transgenic species thereof. In a preferred embodiment, the subject is a human.

The term "administering" includes routes of administration which allow the active ingredient of the invention to perform their intended function.

The term "treat" or "treatment" refers to a method of reducing the effects of a disease or condition. Treatment can also refer to a method of reducing the underlying cause of the disease or condition itself rather than just the symptoms. The treatment can be any reduction from native levels and can be, but is not limited to, the complete ablation of the disease, condition, or the symptoms of the disease or condition.

The term "inhibit," "inhibition," "inhibiting," "prevent," "prevention" or "preventing" means ameliorating, inhibiting or averting from symptoms associated with the target disease or resulted by the target biological mechanism.

The term "cancer" or "cancer cell" refers to diseases in which abnormal cells divide without control and can invade nearby tissues, including carcinoma, sarcoma, leukemia, lymphoma and multiple myeloma, etc. Embodiments of a cancer include but are not limited to invasive breast carcinoma, adenocarcinoma, lung cancer (non-small cell, squamous cell carcinoma, adenocarcinoma, and large cell lung cancer), liver cancer, colorectal cancer, brain, head and neck cancer (e.g., neuro/glioblastoma), breast cancer, ovarian cancer or carcinoma, transitional cell carcinoma of the bladder, prostate cancer, oral squamous cell carcinoma, bone sarcoma, adrenocortical cancer, gastrointestinal tumors including colorectal cancer, biliary tract cancer such as gallbladder carcinoma (GBC), bladder cancer, esophageal cancer, gastric cancer, cervical cancer, salivary gland cancer, diarrhea benign neoplasm, ductal carcinoma in situ, paronychia, cholangiocarcinoma, kidney cancer, pancreatic cancer, medulloblastoma, glioblastoma, luminal, HER2-positive and triple negative mammary tumors, hematologic malignancies or leukemia (acute myelogenous leukemia (AML), B-precursor cell acute lymphoblastic leukemia (ALL), a fraction of T-cell ALL, and chronic myelogenous leukemia (CML).

The phrase "therapeutically effective amount" refers to that amount of a compound, material, or composition comprising a compound of the present invention which is effective for producing a desired therapeutic effect, at a reasonable benefit/risk ratio applicable to any medical treatment.

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: g (grams); mg (milligrams); mL (milliliters); µL (microliters); mM (millimolar); M (micromolar); Hz (Hertz); MHz (megahertz); mmol (millimoles); hr or hrs (hours); min (minutes); MS (mass spectrometry); ESI (electrospray ionization); TLC (thin layer chromatography); and HPLC (high pressure liquid chromatography). For all of the following examples, standard work-up and purification methods known to those skilled in the art can be utilized. Unless otherwise indicated, all temperatures are expressed in ° C. (degrees Centigrade). All reactions are conducted at room temperature unless otherwise noted. Synthetic methodologies illustrated herein are intended to exemplify the applicable chemistry through the use of specific examples and are not indicative of the scope of the disclosure.

In particular, the present invention provides a compound of formula (I):

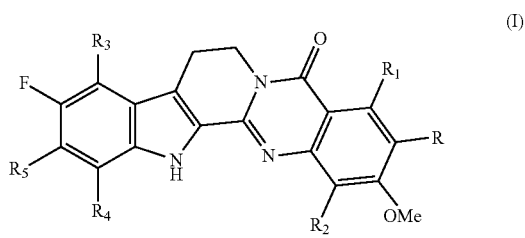

wherein R represents H or methoxy;
$R_1$ and $R_2$ each independently selected from H, hydroxyl, halogen, $C_{1-3}$ alkyl and $C_{1-3}$ alkoxy;
$R_3$ to $R_5$ each independently selected from H, hydroxyl, fluoro, $C_{1-3}$ alkyl and $C_{1-3}$ alkoxy;
or a solvate, prodrug, stereoisomer, enantiomer, or pharmaceutically acceptable salt thereof.

In one embodiment, in formula (I), R is methoxy. In another embodiment, $R_3$ to $R_5$ each are H. In yet another embodiment, $R_1$ and $R_2$ each are H.

In one embodiment, in formula (I), R is H. In another embodiment, $R_3$ to $R_5$ each are H. In yet another embodiment, $R_1$ and $R_2$ each are H.

In a specific embodiment, in formula (I), R is methoxy, $R_1$ to $R_5$ each are H, i.e., the compound 10-fluoro-2,3-dimethoxyrutaecarpine. In another specific embodiment, in formula (I), R and $R_1$ to $R_5$ each are H, i.e., the compound 10-fluoro-2-methoxyrutaecarpine (F-RUT).

The compounds of Formula (I) of the present invention are prepared according to general chemical synthetic procedures. The preparation of the embodiments of the compounds of the present invention is illustrated below. Suitable syntheses for compounds of the invention can be found in the Examples below.

In one aspect, the compound of formula (I) is synthesized via the schemes below:

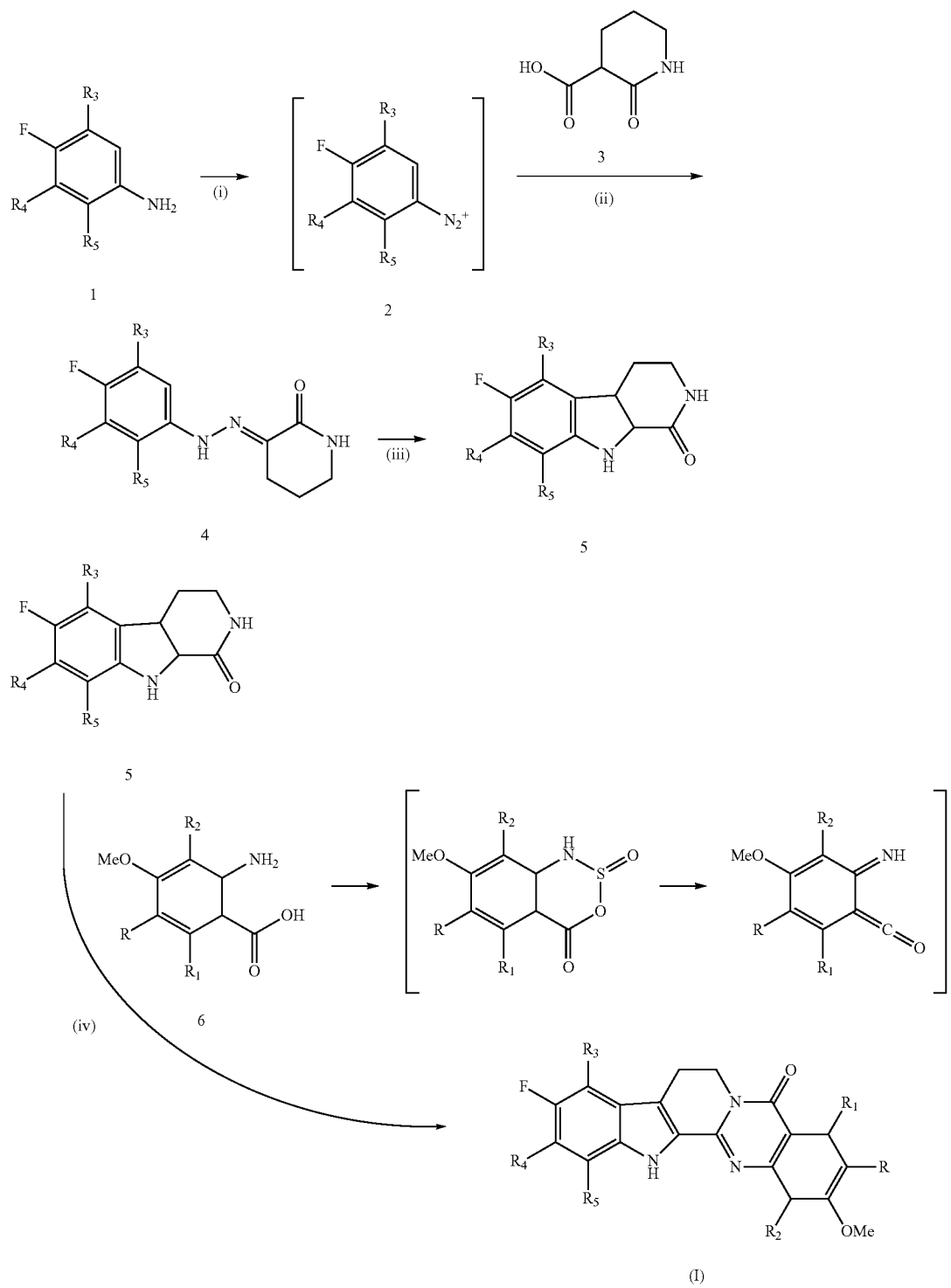

wherein condition (i) represents the presence of NaNO$_2$/HCl at 0° C., condition (ii) represents the presence of acetic acid at 0° C., condition (iii) represents the presence of formic acid at reflux and condition (iv) represents the presence of SOCl$_2$/toluene.

In another aspect, the invention provides a pharmaceutical composition comprising a compound of formula (I), or a pharmaceutically acceptable ester, salt, or prodrug thereof, together with a pharmaceutically acceptable carrier.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gel caps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above.

The liquid forms in which the novel compositions of the present invention may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

Tablets and capsules for oral administration are normally presented in unit dose form and contain conventional excipients such as binders, fillers (including cellulose, mannitol, lactose), diluents, tableting agents, lubricants (including magnesium stearate), detergents, disintegrants (e.g. polyvinylpyrrolidone and starch derivatives such as sodium glycolate starch), coloring agents, flavoring agents, and wetting agents (for example sodium lauryl sulfate).

The oral solid compositions can be prepared by conventional methods of blending, filling or tableting. The blending operation can be repeated to distribute the active principle throughout compositions containing large quantities of fillers. Such operations are conventional.

For parenteral administration fluid unit dosages can be prepared, containing the compound and a sterile vehicle. The compound can be either suspended or dissolved, depending on the vehicle and concentration. The parenteral solutions are normally prepared by dissolving the compound in a vehicle, sterilizing by filtration, filling suitable vials and sealing. Advantageously, adjuvants such as local anaesthetics, preservatives and buffering agents can also be dissolved in the vehicle. To increase the stability, the composition can be frozen after having filled the vials and removed the water under vacuum. Parenteral suspensions are prepared in substantially the same manner, except that the compound can be suspended in the vehicle instead of being dissolved, and sterilized by exposure to ethylene oxide before suspending in the sterile vehicle. Advantageously, a surfactant or wetting agent can be included in the composition to facilitate uniform distribution of the compound of the application.

Pharmaceutical preparation for administration by inhalation can be delivered from an insufflator or a nebulizer pressurized pack.

In one aspect, the present invention provides a method of ameliorating inflammation in a subject, comprising a step of administering a compound as disclosed herein to the subject.

In another aspect, the present invention provides a method of suppressing nitrogen oxide (NO) release in a subject, comprising a step of administering a compound as disclosed herein to the subject.

In another aspect, the present invention provides a method of suppressing TNF-α release in a subject, comprising a step of administering a compound as disclosed herein to the subject.

In another aspect, the present invention provides a method of inhibiting cell migration, cell invasion or both in a subject, comprising a step of administering a compound as disclosed herein to the subject.

In another aspect, the present invention provides a method of ameliorating damage due to remodeling between the epithelium and endothelium in a subject, comprising a step of administering a compound disclosed herein to the subject.

In another aspect, the present invention provides a method of reducing Snail Protein levels in a subject, comprising a step of administering a compound as disclosed herein to the subject.

In another aspect, the present invention provides a method of improving cardiac, vasodilation and/or lung functions of a subject, comprising a step of administering a compound as disclosed herein to the subject. Preferably, the improvement comprises inhibition of fibrosis of heart, blood vessels and/or lung.

The compounds, or pharmaceutically acceptable salts thereof, are administered orally, nasally, transdermally, pulmonary, inhalationally, buccally, sublingually, intraperintoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

The invention having now been described by way of written description, those of skill in the art will recognize that the invention can be practiced in a variety of embodiments and that the foregoing description and examples below are for purposes of illustration and not limitation of the claims that follow.

EXAMPLES

All the key raw materials were purchased from various commercial sources and used without further purification. Some of the key raw materials and reagents were available in-house.

Synthetic Example 1

The compounds 10-fluoro-2-methoxyrutaecarpine (F-RUT) and 10-fluoro-2,3-dimethoxyrutaecarpine are synthesized via the following scheme:

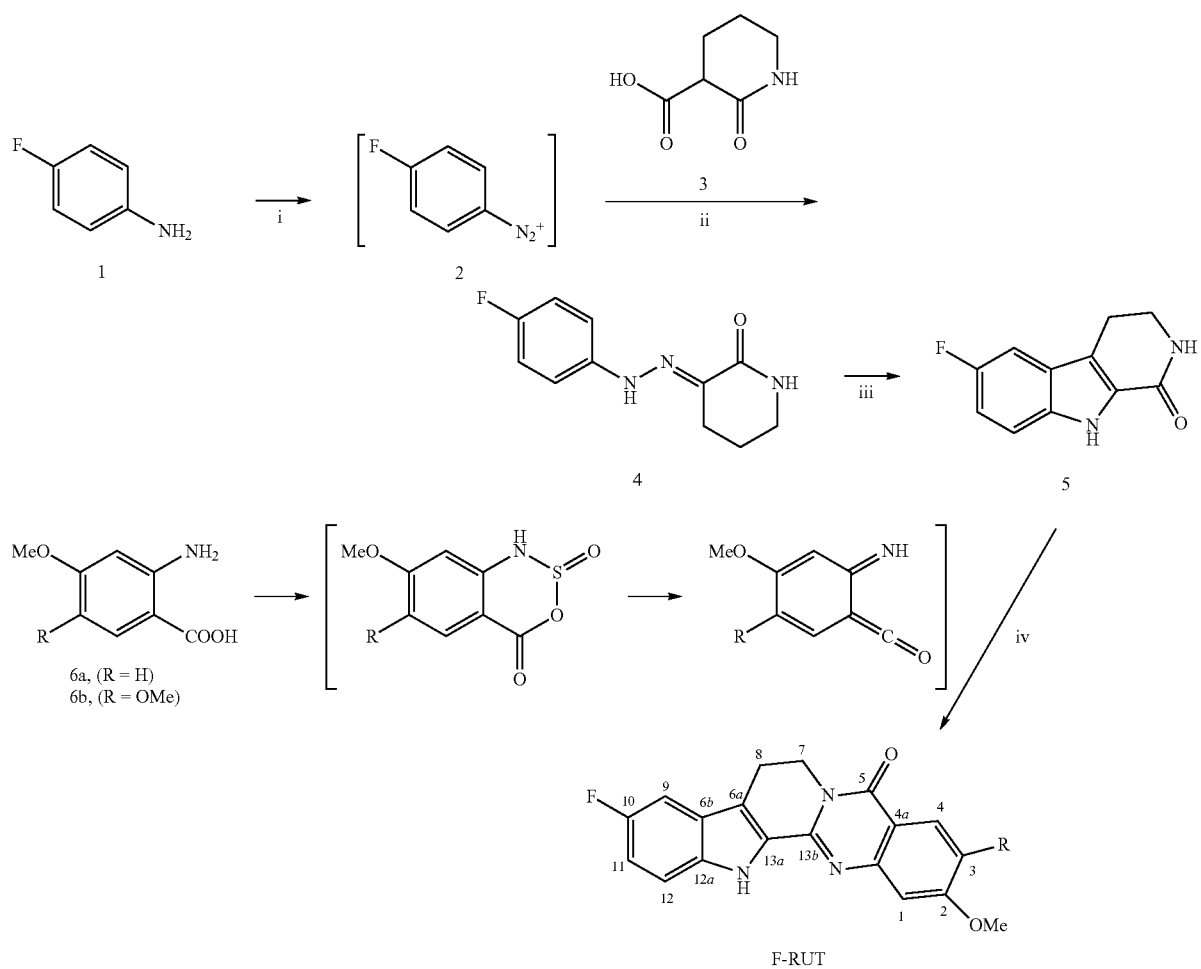

R = H (F₂ₘₒ-RUT)
R = OMe (F₂ₘₒ-RUT)
35~40%

Aniline (1) was subjected to the Sandmeyer reaction to give the diazonium salt, which was then coupled to a carboxylic acid (3) to yield hydrazone (4), and treatment of the hydrazone (4) in an acidic condition gave the carboline (5) in a 58% yield (three steps). The carboline (5) was then coupled with in-situ activated substituted o-aminobenzoic acid derivatives (6a,b), which were pretreated with thionyl chloride in the presence of toluene at 70-80° C. to provide 10-fluoro-2-methoxyrutaecarpine (F-RUT) and 10-fluoro-2,3-dimethoxyrutaecarpine in 35% and 40% overall yields (four steps), respectively.

The synthetic products were identified by $^1$H and $^{13}$C nuclear magnetic resonance (NMR), infrared (IR), and mass spectrometry (MS). For F-RUT, FT-IR (KBr, cm$^{-1}$): 3347 (N–H) and 1652 (carbonyl group). $^1$H-NMR (CDCl$_3$, ppm): δ 3.18 (t, J=6.9 Hz, 2H, 2H-8), 4.57 (t, J=6.9 Hz, 2H, H–7), 3.93 (s, 3H, 2-OMe), 7.02 (dd, J=8.9, 2.4, 1H, H–3), 7.05 (d, J=2.4, 1H, H–1), 8.21 (d, J=8.9, 1H, H–4), 7.11 (d, J=8.8, 1H, H–12), 7.38 (d, J=8.8, 1H, H–11), 8.99 (s, 1H, H–9), 12.04 (s, 1H, N–H). MS-ESI (m/z) ([M-H]$^-$): calcd. 335.3; found 334.4. For 10-fluoro-2,3-dimethoxyrutaecarpine (F$_{2MO}$-RUT), FT-IR (KBr, cm$^{-1}$): 3398 (N–H) and 1641 (carbonyl group). $^1$H-NMR (CDCl$_3$, ppm): δ 3.18 (t, J=6.8 Hz, 2H, H–8), 4.57 (t, J=6.8 Hz, 2H, H–7), 3.92 (s, 3H, O-Me), 3.88 (s, 3H, O-Me), 7.04 (s, 1H, H–1), 7.11 (d, J=8.9, 1H, H–12), 7.37 (d, J=8.9, 1H, H–11), 7.66 (s, 1H, H–4), 8.94 (s, 1H, H–9), 11.87 (s, 1H, N–H). MS-ESI (m/z) ([M-H]$^-$): calcd. 365.3; found 364.4.

Biological Assay

Preparation Example 2—Cell Culture

The RAW264.7 macrophage cell line and A2780 ovarian carcinoma cells were grown in Dulbecco's modified Eagle medium (DMEM) containing 10% fetal bovine serum (FBS), 100 U/mL penicillin, 100 μg/mL streptomycin, 1 mM sodium pyruvate, 4.5 g/L glucose, 4 mM 1-glutamine, and 1.5 g/L sodium bicarbonate at 37° C. in a humidified atmosphere with 5% CO2. Primary human aortic ECs (HAECs) were grown in a MesoEndo Endothelial Cell Growth Medium Kit (Cell Applications, San Diego, Calif., USA) supplemented with 10% FBS at 37° C. in a humidified atmosphere with 5% CO2.

Example 3—Suppression of NO and TNF-Alpha Releases by LPS-Treated Cells

NO production was evaluated by measuring the nitrite concentration in supernatants of cultured RAW264.7 macrophages. Cells were first seeded at a density of 2×10⁵ cells/mL in 24-well plates for 24 h, followed by co-treatment with different concentrations of F-RUT with lipopolysaccharide (LPS) (40 ng/mL) for another 24 h. The amount of nitrite in cell culture supernatants was detected using the Griess reagent (1% sulfanilamide in 5% phosphoric acid and 0.1% naphthylethylenediamine dihydrochloride in water). Data are reported as the mean±standard error of the mean (SEM) values of three independent determinations.

Figure 1B:
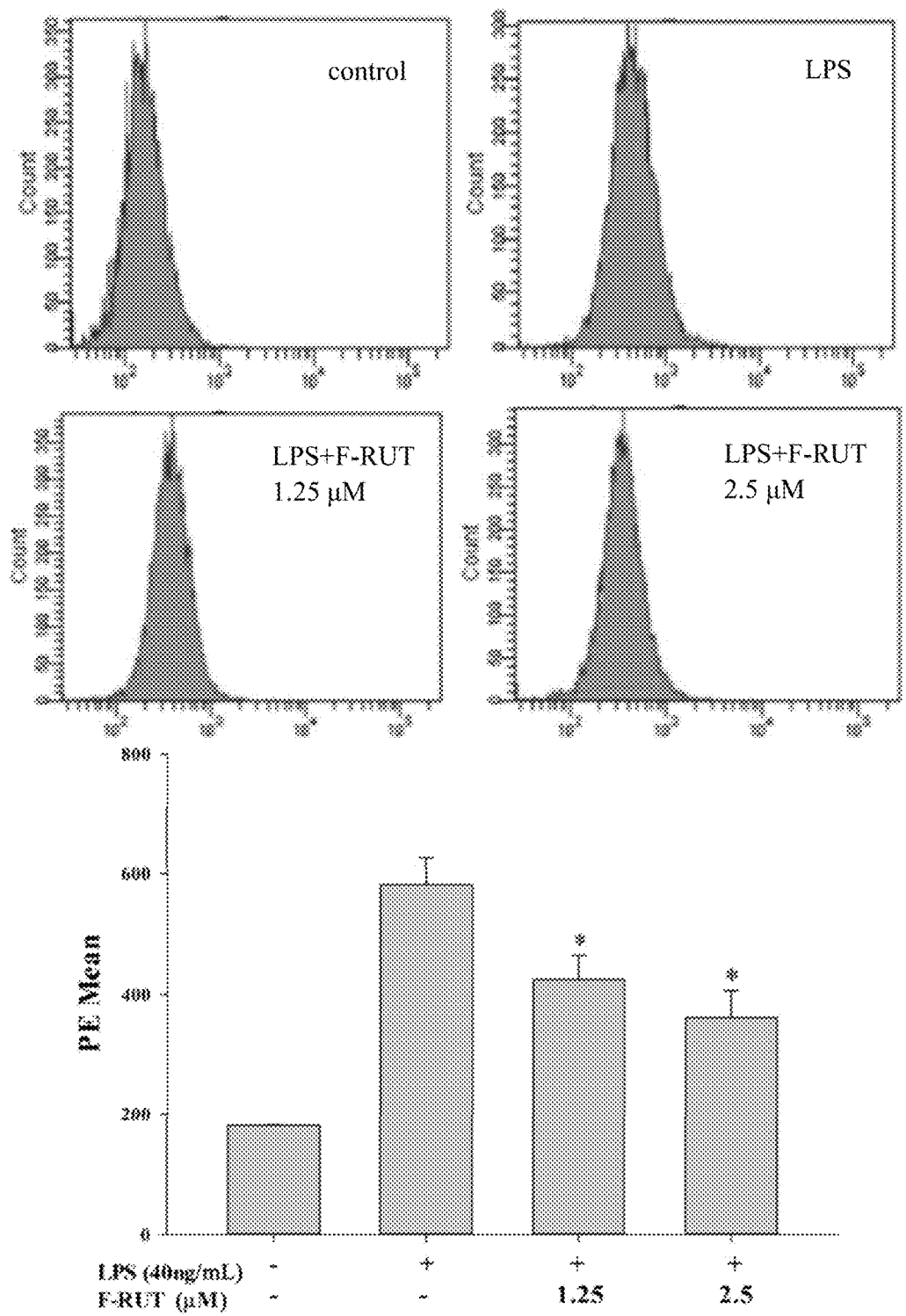
Figure 1C:
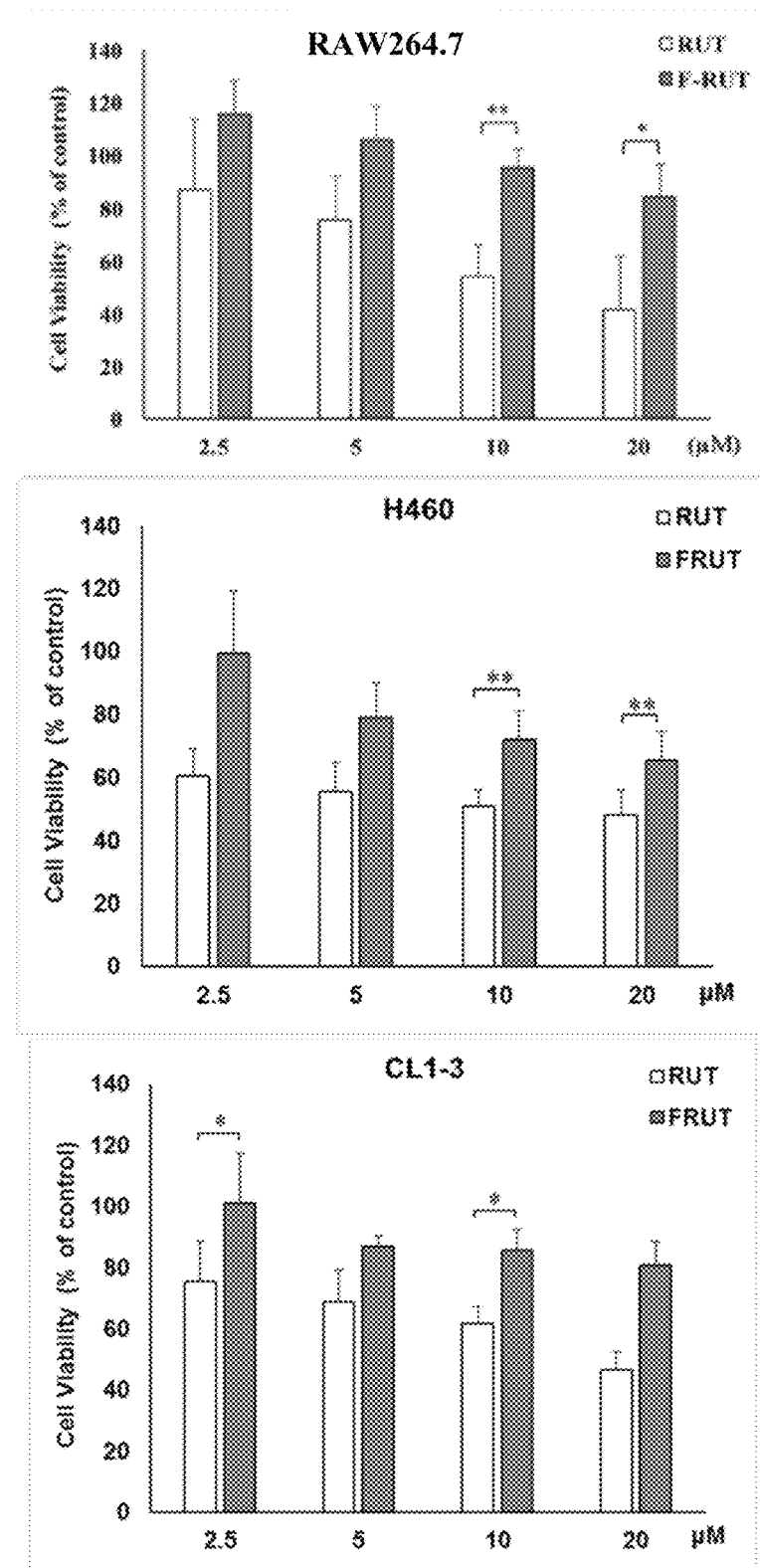

NO production of LPS-treated RAW264.7 macrophages increased compared to that of untreated cells. Co-treatment with the synthesized F-RUT suppressed NO production in a concentration-dependent (0-20 μM) manner (*p<0.05, **p<0.01, compared to the LPS-treated group) (FIG. 1(a)). A consistent concentration-dependently potent (*p<0.05, compared to the LPS-treated group) (FIG. 1(b)) suppressive effect of TNF-α released into the medium was also shown. The suppressive effects were not due to cytotoxic activity because F-RUT showed substantially no cytotoxicity to RAW264.7, H460 and CL1-3 cells at concentrations of 0-20 μM (*p<0.05, **p<0.01, compared to the RUT-treated group) (FIG. 1(c)).

Example 4—Suppression of Inducible (i)NOS and COX-2 Expressions

An MTT assay to test cell viability was performed based on the conversion of the yellow tetrazolium salt to the purple formazan product. Cells (104 cells/well) were grown in a 96-well plate supplemented with standard culture medium. Cells were treated with RUT and F-RUT (0-20 μM) for 24 h. An MTT stock solution (5 mg of MTT/mL of phosphate-buffered saline; PBS) was added to the growing cultures for 2 h. The absorbance was measured with a spectrophotometer at 560 nm. DMSO alone was measured as a reading control. Data were reported as the mean±SEM values of five independent determinations.

Protein samples were separated and resolved by sodium dodecylsulfate polyacrylamide gel electrophoresis (SDS-PAGE) and electrotransferred onto a polyvinylidene difluoride (PVDF) membrane. The membrane was incubated with a primary antibody at 4° C. overnight, and then incubated with a horseradish peroxidase (HRP)-conjugated secondary immunoglobulin G (IgG) antibody; immunoreactive bands were visualized with PerkinElmer enhanced chemiluminescent reagents.

RAW264.7 macrophages were seeded in a 96-well plate with DMEM. Then, cells were transfected with the pGL4.32 [luc2P/NF-κB-RE/Hygro] (Promega, Madison, Wis., USA) plasmid reporter gene using TurboFect Transfection Reagent (Fermentas, Glen Burnie, Md., USA). At 24 h after transfection, cells were treated with LPS (40 ng/mL) and F-RUT for 24 h in serum-free medium. Then the luciferase activity was detected by the luminescence measured in a luminescence microplate reader (Thermo Varioskan Flash, Waltham, Mass., USA) using a ONE-Glo luciferase assay kit (Promega). Luciferase activities were normalized to protein concentrations.

Figure 2A:
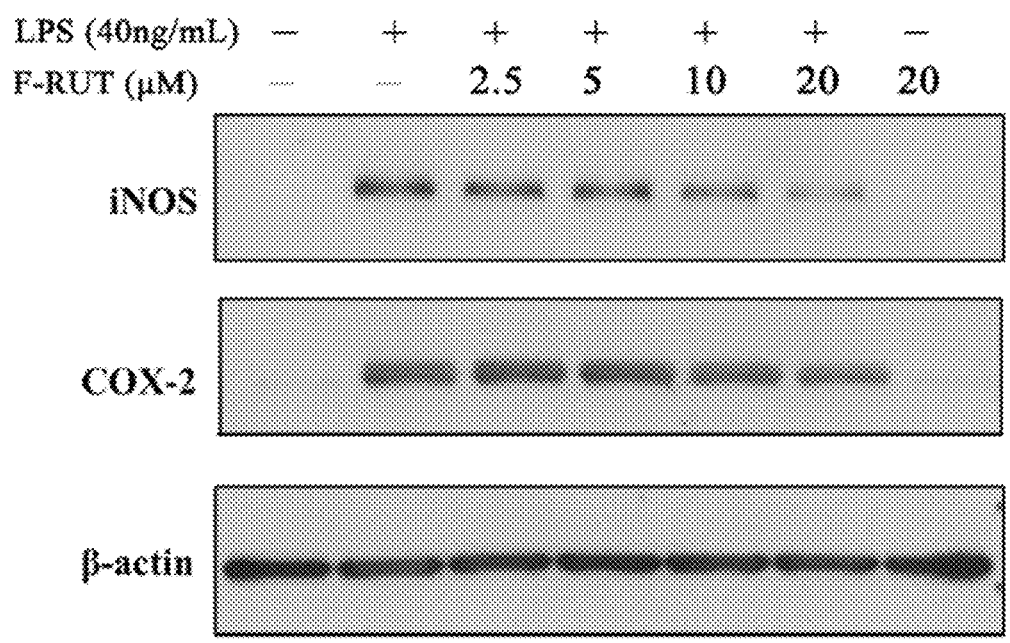
FIGS. 2A and 2B show the effect of 10-fluoro-2-methoxy-rutaecarpine (F-RUT) on inducible nitric oxide synthase (iNOS) and cyclooxygenase (COX)-2 expressions by lipopolysaccharide (LPS)-treated RAW264.7 macrophages: (a), and luciferase reporter plasmid-transfected macrophages (b). Cells were transfected with 2.5 μg of the pGL4.32 [luc2P/NF-κB-RE/Hygro] reporter plasmid, then treated with different concentrations of F-RUT and LPS (40 ng/mL) for 24 h. Levels of luciferase activity were determined as described in Materials and Methods. Values are expressed as the mean±SE of triplicate tests. *p<0.05, **p<0.01 versus LPS treatment.
Figure 2B:
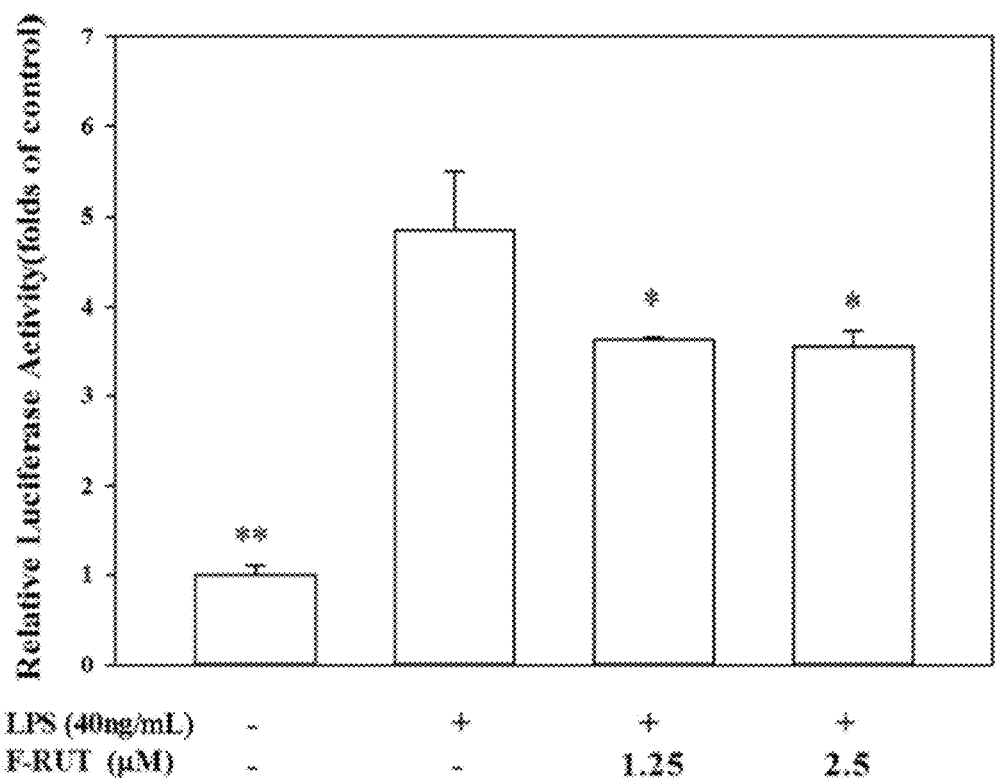

The inventors observed that LPS-treated RAW264.7 macrophages exhibited significantly elevated protein amounts of iNOS and COX-2, while F-RUT suppressed their expressions in a concentration-dependent manner (FIG. 2(a)). β-Actin protein levels of the loading controls remained constant. In the inflammation reaction, NF-κB activation triggers the induction of COX-2 and iNOS. We determined whether F-RUT suppressed NF-κB activation in LPS-activated macrophages. An NF-κB-dependent luciferase reporter plasmid was transiently transfected in LPS-induced macrophages to confirm whether F-RUT inhibited NF-κB-binding activity. F-RUT inhibited LPS-induced NF-κB transcriptional activity at 0-2.5 μM (*p<0.05, **p<0.01, compared to the LPS-treated group) (FIG. 2(b)). The results suggested that inhibition of iNOS and COX-2 expression by F-RUT was correlated with suppression of NF-κB activation. The inventors also observed that, in addition to COX-2 suppression, the enzyme activity is also inhibited. Compared to RUT, F-RUT showed less cytotoxicity, but retained the anti-inflammatory activity.

Example 5—Inhibition of Cell Migration/Invasion

A2780 cells were cultured at a density of 2×10⁵ cells/well in 6-well plates and incubated at 37° C. for 24 h. A centerline in the cells was scratched using a 200-μL pipette tip and washed with PBS. Then, new complete medium was added and treated with or without 1 and 2.5 μM of F-RUT for 24 h. At the endpoint of incubation, cells were examined and photographed with an optical microscope. The distance between the edges of the scratched area was measured and calculated to estimate the migratory ability of cells.

A2780 cell invasion was evaluated using 24-well transwell inserts (8-μm-pore filters, Merck Millipore) individually coated with Matrigel (BD Biosciences, Bedford, Mass., USA). A2780 cells (2×104 cells in each well) were cultured for 24 h with serum-free minimum essential medium (MEM) and then treated with F-RUT (1.25 or 2.5 μM) for another 24 h in the upper chamber of the transwell. Medium containing 10% FBS was placed in the lower chamber. At the end of incubation, non-migrated cells were removed using a cotton swab; cells that had penetrated to the opposite surface of the filter were fixed with 4% formaldehyde and stained with 2% crystal violet. Stained cells were counted and photographed under a phase-contract optical microscope at 200× magnification. Three independent experiments were performed as described elsewhere.

Figure 3A:
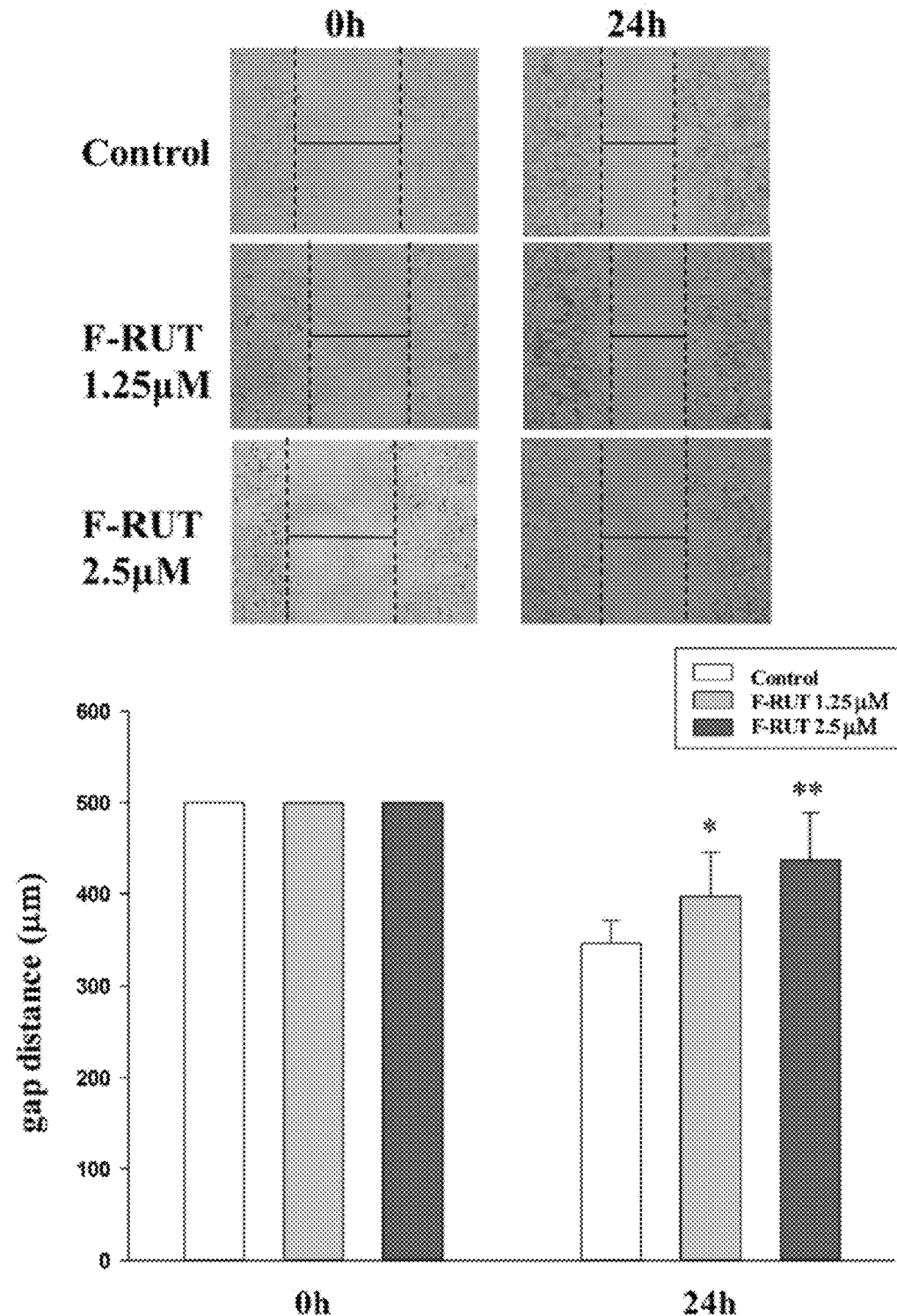
FIGS. 3A and 3B show the effects of 10-fluoro-2-methoxyrutaecarpine (F-RUT) on migration and invasion: Cell migration (a) and cell invasion (b) were detected following F-RUT treatment for 0-24 h, and photographed with a microscope (upper panel). The statistical analysis is shown in the lower panel. (*p<0.05, **p<0.01).
Figure 3B:
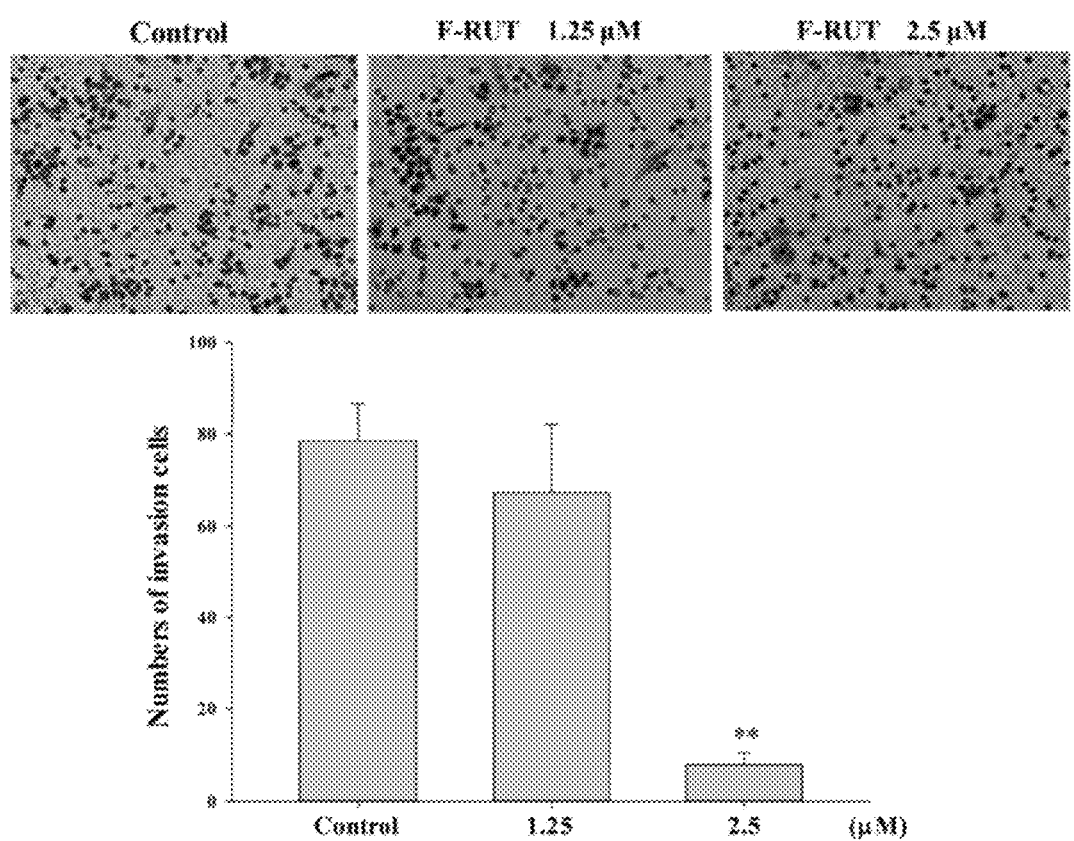

As illustrated in FIG. 3(a), wound-healing assays used an ovarian carcinoma A2780 cell line in the presence of F-RUT (0-5 μM) for 0-24 h. The migration rate was measured using imaging software, and Student's t-test was used for the statistical analysis. F-RUT showed significant effects against cell migration. F-RUT (0-2.5 μM) treatments for 24 h also exhibited invasion inhibitory activity in a transwell assay (FIG. 3(b)).

Example 6—Activation of TRPV1 and eNOS

Figure 4:
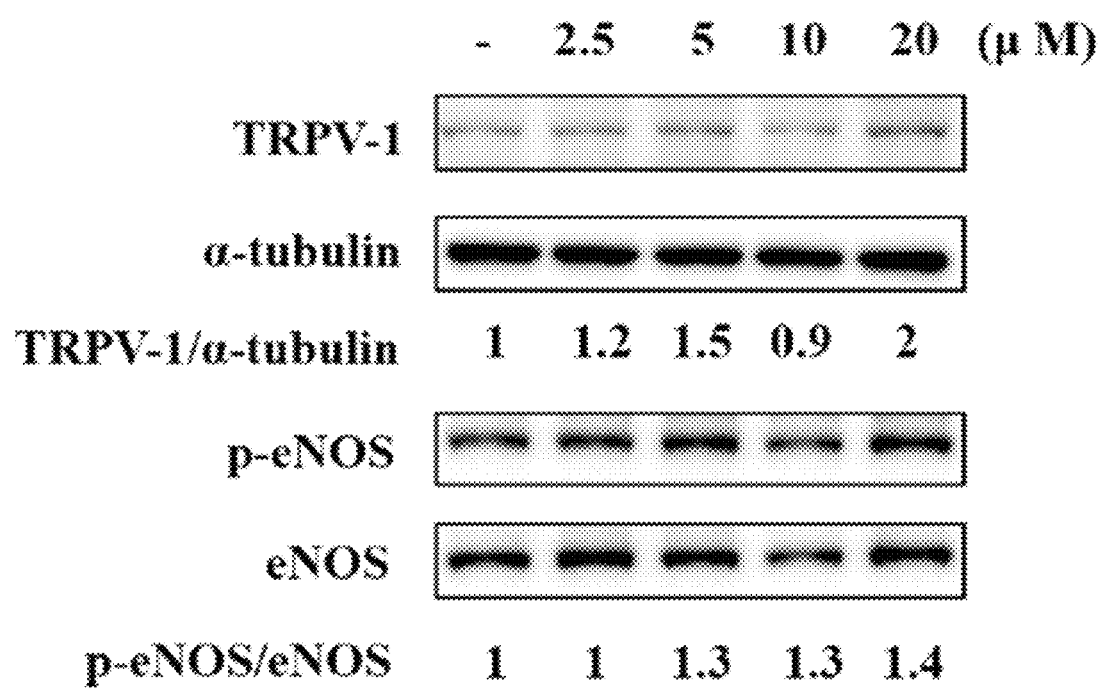
FIG. 4 shows the effects of 10-fluoro-2-methoxyrutaecarpine (F-RUT) on transient receptor potential vanilloid-type 1 (TRPV-1) expression and endothelial nitric oxide synthase (eNOS) phosphorylation in human aortic endothelial cells (HAECs). The densitometric ratio is indicated.

TRPV1 is reportedly present in ECs of arteries. To validate the expression of TRPV1 in the endothelium, the TRPV1 protein of human aortic ECs (HAECs) was detected using immunoblotting; the method of Western Blot Analysis has been stated in Example 4. F-RUT treatment (20 μM) for 15 min increased TRPV1 protein amounts two-fold compared to the control group after normalization with α-tubulin levels (FIG. 4). The effect of F-RUT on the phosphorylation of eNOS in HAECs is further examined because NO production is consequently regulated by the phosphorylation of eNOS. F-RUT treatment (20 μM) for 15 min significantly increased the phosphorylation of eNOS 1.4-fold compared to the control group after normalization with total eNOS (lower panel). F-RUT upregulated the expression of TRPV1 and activated eNOS phosphorylation in ECs.

Animal Experiment

Example 7—Amelioration of Inflammation in OVA/Alum-Challenged Mice

BALB/c mice (six weeks of age) were obtained from the Animal Center of the College of Medicine, National Taiwan University (Taipei, Taiwan), and sensitized with an intraperitoneal injection of 20 μg of ovalbumin (OVA) emulsified in 2 mg of aluminum hydroxide in a total volume of 200 μL phosphate-buffered saline (PBS) on day 0, and boosted with 50 μg of OVA emulsified in 4 mg of aluminum hydroxide on days 14 and 28. RUT or F-RUT was given by oral administration on days 30, 32, 34, 36, and 38. For post-challenge, all mice were treated intranasally with OVA (100 μg in a total volume of 40 μL PBS) on days 40, 41, 42, and 43. At 24 h after the last OVA challenge, mice were sacrificed, and their organs were collected. All experimental procedures were reviewed and approved by the Institutional Animal Care and Use Committee or Panel. Lung tissues were fixed in 4% paraformaldehyde (sc-281692; Santa Biotechnology) and embedded in paraffin. Tissue sections were made at a 5-μm thickness, and stained with hematoxylin and eosin (H&E) solution for examination of inflammation.

Figure 5A:
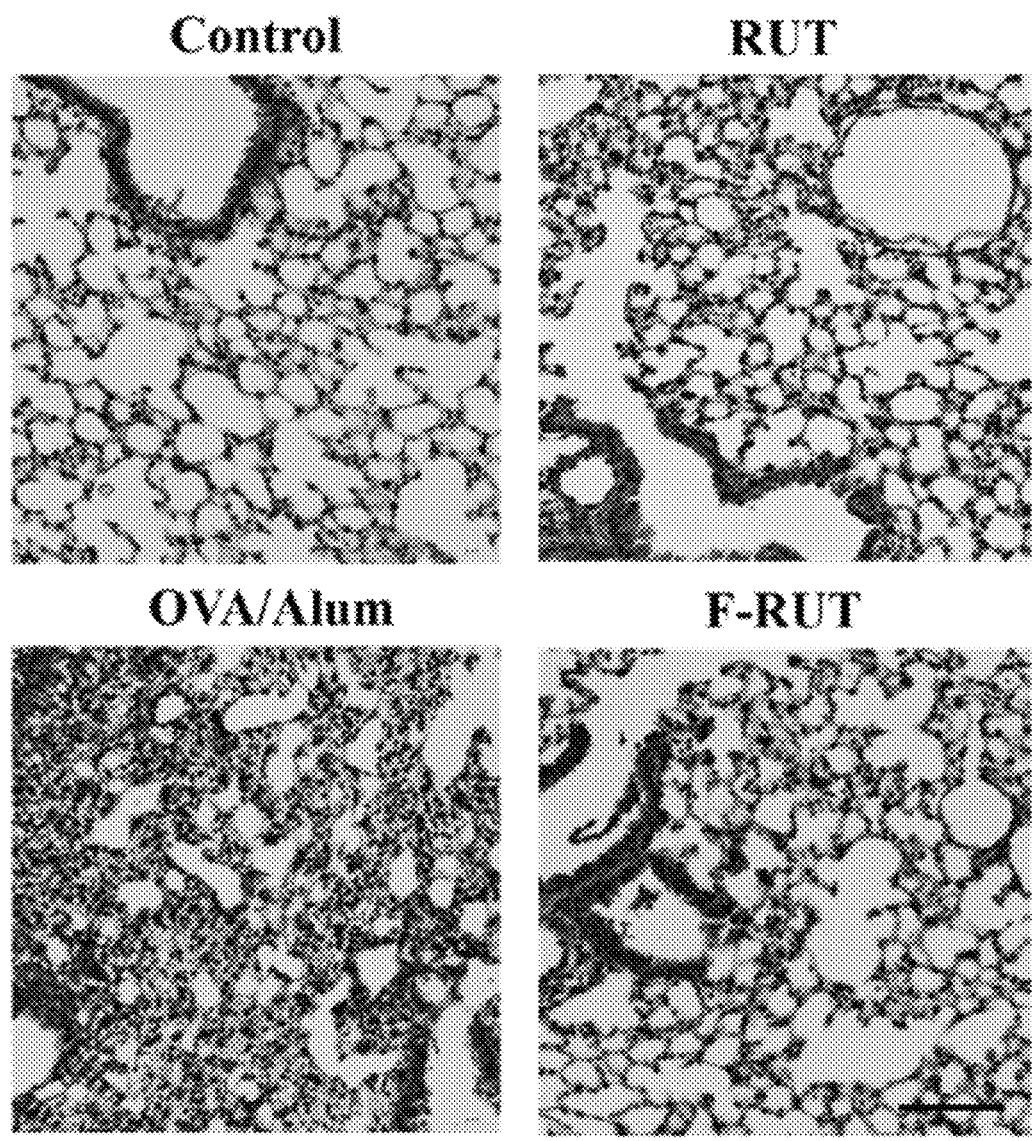
FIG. 5A thru 5C show the effects of 10-fluoro-2-methoxy-rutaecarpine (F-RUT) on ovalbumin (OVA)-challenged mice: (a) BALB/c mice as target animals, (b) KLF10 KO mice as target animals, (c) collagen formation around the bronchus of KLF10 KO mice. Data are representative of three to five mice per group. Scale bar is 100 μm.

There was predominant inflammation in the lungs accomplished by increased infiltrating neutrophils after mice had been challenged with OVA/alum for 44 days. Alternate-day oral administration of RUT or F-RUT ameliorated the OVA/alum-induced lung inflammation and showed a similar pattern to the untreated control group (FIG. 5(a)).

Figure 5B:
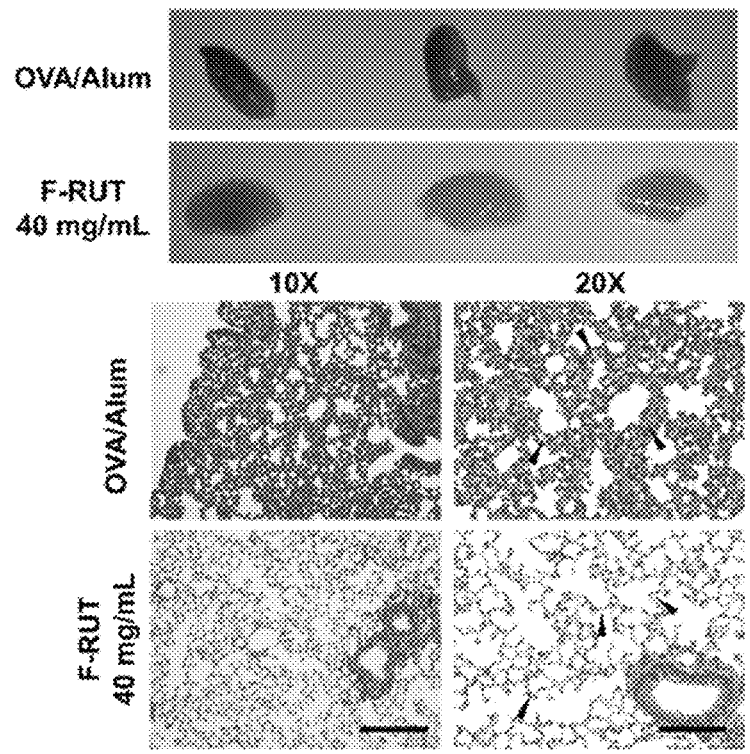
Figure 5C:
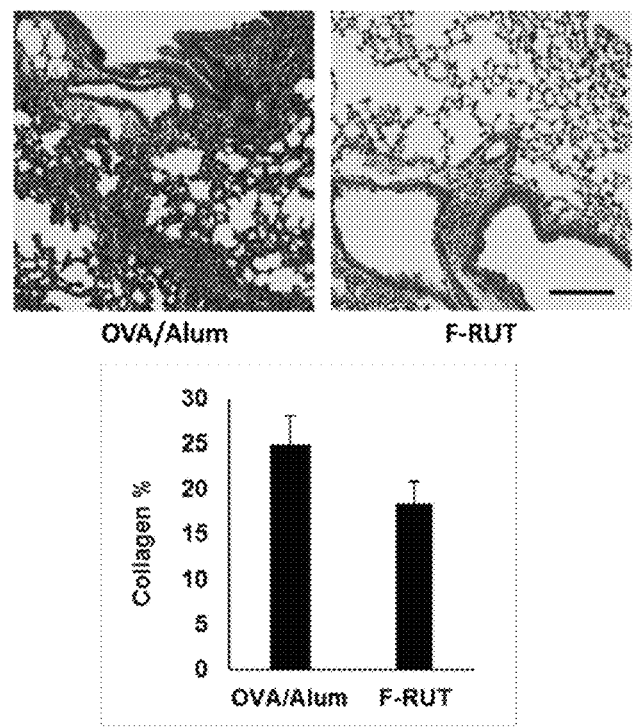

KLF10 gene is regulated by transforming growth factor (TGF)-β/Smad. Deletion of Klf10 in mice is associated with significant inflammation of the lungs challenged with OVA/alum for 44 days. In another experiment, KLF-10 KO mice was used. There was predominant inflammation in the mice lungs accomplished by increased infiltrating neutrophils after challenged with OVA/alum for 44 days. Alternate-day oral administration of F-RUT ameliorated the OVA/alum-induced lung inflammation (FIG. 5(b)). The collagen formation around the bronchus was decreased after the oral administration of F-RUT (25% in OVA/Alum group, 18% in F-RUT group)(FIG. 5(c)). These results suggest the beneficial effect of F-RUT on inflammation induced fibrosis.

Figure 6:
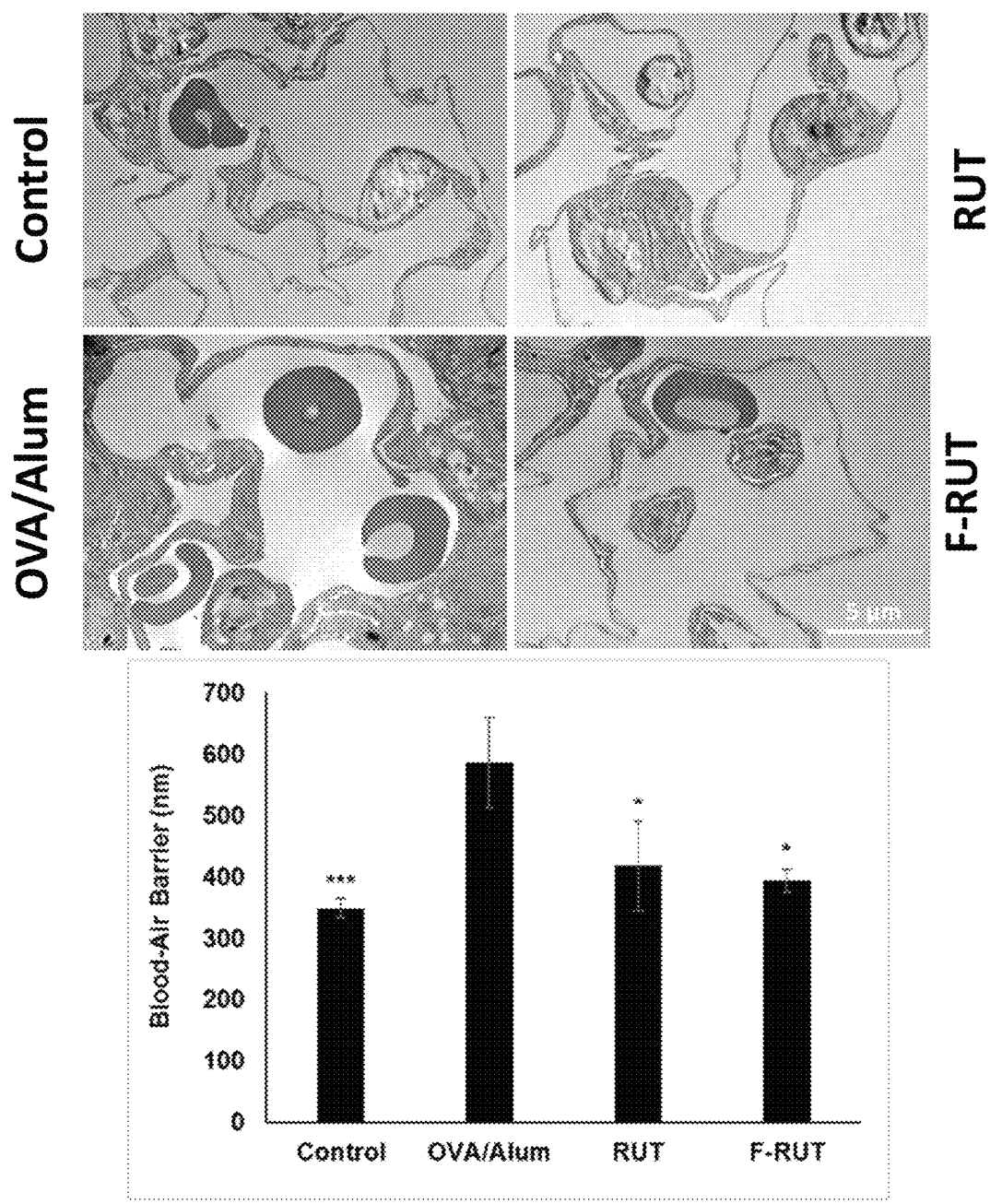
FIG. 6 shows the average thickness of blood-air-barrier in the tests of KLF10 KO mice.

Example 8—Amelioration of Inflammation-Stimulated Respiratory Interface in KLF10 KO Mice Blood-Air-Barrier (alveolar-capillary membrane), gas exchanging region of the lungs, was measured to perform the lung function. After the KLF-10 KO mice were challenged with OVA/Alum and oral administration of RUT or F-RUT, the lung was harvested to measure the thickness of blood-air-barrier by TEM. The average thickness of blood-air-barrier was significant increased in OVA/Alum group (586 nm compared to 348 nm in control group) and reversed by RUT or F-RUT (418 and 393 nm, respectively), see FIG. 6. These data explored the potential biological function of F-RUT in protecting lung from inflammation.

Example 9—Inhibition of ROS Activity in Zebrafish

Figure 7:
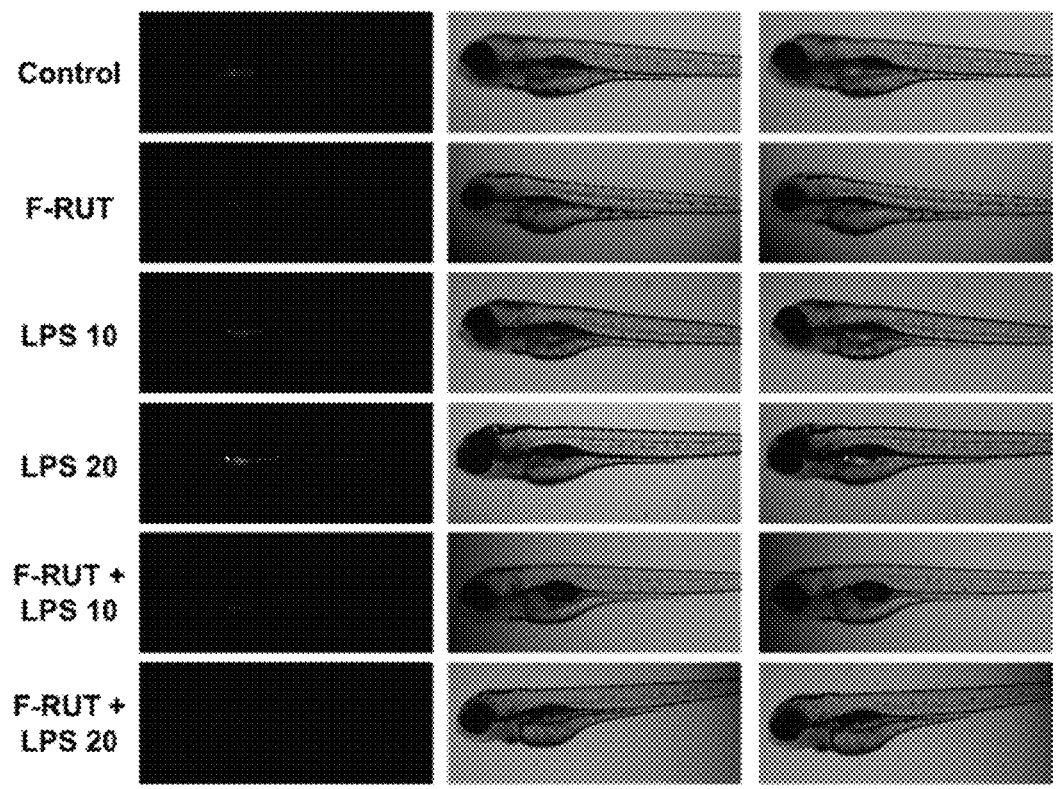
FIG. 7 shows the ROS inhibition activity in Zebrafish.
Figure 7:
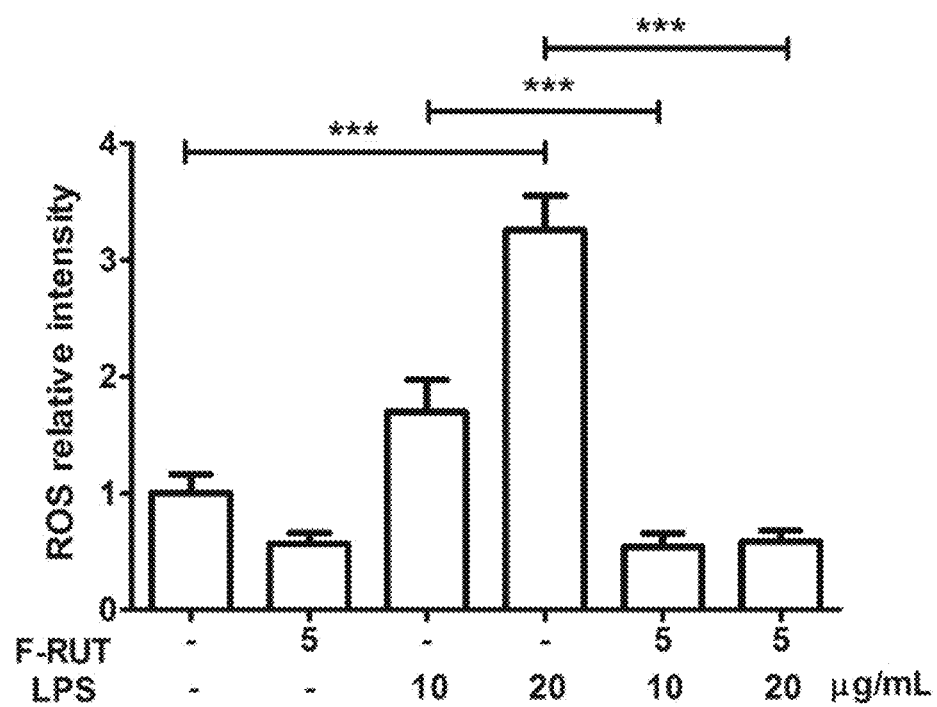

FIG. 7 shows that the anti-inflammation effects of F-RUT not only in cell but also in zebrafish model. LPS significantly induced ROS level in zebrafish at 10 and 20 ng/ml (*$p<0.001$, compared to control group). 5 ng/ml F-RUT suppressed the LPS-induced ROS as similar level to the group treated with F-RUT only (*$p<0.001$, compared to LPS group).

The inventors find the following phenomena to evidence the claimed effect.

First, vasodilator effects of RUT to induce CGRP synthesis and release were via activation of TRPV1. Therefore, RUT's analogs were designed and synthesized for better vasodilator effects. Structural modifications of RUT were designed to enhance its biological activities. However, increased cytotoxicity hampers their application in vascular disorders. Fluorinated RUT, novel analogs provided herein with very low cytotoxicity, showed anti-inflammatory activity (Examples 7 to 9) and migration/invasion-suppressive activities (Example 5) that are beneficial in reducing side effects when used for pharmaceutics. In addition, eNOS and iNOS are isoforms with identical promoter elements that drive similar biological effects. With respect to the diverse effects of fluorinated RUT on eNOS and iNOS described herein, they could have resulted from different signaling pathways in macrophages and ECs. Fluorinated RUT suppressed iNOS in macrophages, while it activated eNOS in Ecs (Examples 4 and 6). The results bolster Fluorinated RUT, derived from RUT, having enhanced beneficial effects and reduced adverse effects.

OVA/alum-sensitized mice are a well-known animal model to induce lung inflammation. In the airways, there are increased granulocytes, for example, neutrophils, and remodeling of the interstitium (capillary endothelium, alveolar epithelium, basement membrane, and perivascular tissue). Here, the examples showed that fluorinated RUT reduced infiltrating neutrophils and maintained the air sac structure in OVA/alum-challenged mice (Example 7). These results might imply not just an anti-inflammatory effect but its benefit against damage due to remodeling between the epithelium and endothelium as well.

Hypertension activates pro-oxidant enzymes resulting in increased ROS formation, which is associated with Ang-II and mechanical forces, and damage to the vasculature. Inflammation, migration, and fibrosis are important factors contributing to endothelial dysfunction and cardiovascular remodeling. Oxidative stress plays a physiological role in controlling endothelial function and also a pathophysiological role. Many heart injuries result in fibrosis with deposition of excess collagens, or other matrix proteins, leading to the development of heart failure. Inflammation is the initial and primary trigger in cardiac stress and involves elevated levels of inflammatory cytokines and chemokines in tissues. Fibrosis is characterized by the excess production of ECM produced by myofibroblasts. Cardiac fibroblasts originate from the endothelial-to-mesenchymal transition (EndMT) of ECs, which is important in the formation of cardiac fibroblasts. The EndMT is regulated by signaling pathways mediated by inflammation-associated cytokines. Direct contact with the bloodstream makes the endothelium a promising target for drug treatment. Ischemia/reperfusion injury leading to cardiac fibrosis is mainly mediated by collagen deposition by myofibroblasts. Snail induction is involved in fibrosis when undergoing the EndMT. Snail inhibitors remarkably suppressed collagen deposition and cardiac fibrosis in mice. Fluorinated RUT treatment of A2780 cells produced reduced Snail protein levels, which suggests that inhibition of the EndMT by fluorinated-RUT could be a new strategy for combating vascular diseases (figure not shown).

A previous study illustrated that inflammation and myofibroblast formation contribute to the development of pulmonary fibrosis. Inflammatory cytokines induce the transformation of ECs to myofibroblasts through the EMT, and then produce excess ECM causing fibrosis. Fluorinated-RUT, a class of RUT derivatives, possesses low cytotoxicity but retains its activities against inflammation and migration/invasion. Treatment with fluorinated RUT enhanced TRPV1 and activated eNOS activity. According to the examples provided above, fluorinated RUT would provide applications in improving cardiac, vasodilation, and lung functions.

What is claimed is:

1. A compound having the following Formula (I),

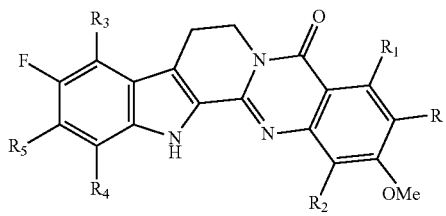

(I)

wherein R represents H or methoxy;
$R_1$ and $R_2$ are each independently selected from H, hydroxyl, halogen, $C_{1-3}$ alkyl and $C_{1-3}$ alkoxy;
$R_3$, $R_4$, and $R_5$ are each independently selected from H, hydroxyl, fluoro, $C_{1-3}$ alkyl and $C_{1-3}$ alkoxy;
or a solvate, prodrug, stereoisomer, enantiomer, or pharmaceutically acceptable salt thereof.

2. The compound of claim 1, wherein R is methoxy.
3. The compound of claim 2, wherein $R_3$, $R_4$, and $R_5$ are each H.
4. The compound of claim 3, wherein $R_1$ and $R_2$ each are H.
5. The compound of claim 1, wherein R is H.
6. The compound of claim 5, wherein $R_3$, $R_4$, and $R_5$ are each H.
7. The compound of claim 6, wherein $R_1$ and $R_2$ each are H.
8. A pharmaceutical composition comprising a compound of claim 1, or a pharmaceutically acceptable ester, salt, or prodrug thereof, together with a pharmaceutically acceptable carrier.
9. A method of ameliorating inflammation in a subject, comprising a step of administering a compound of claim 1 to the subject.
10. A method of ameliorating damage due to remodeling between the epithelium and endothelium in a subject, comprising a step of administering a compound of claim 1 to the subject.
11. A compound of 10-fluoro-2-methoxyrutaecarpine (F-RUT).
12. A compound of 10-fluoro-2,3-dimethoxyrutaecarpine.

* * * * *

UNITED STATES PATENT AND TRADEMARK OFFICE
CERTIFICATE OF CORRECTION

PATENT NO. : 10,526,333 B2
APPLICATION NO. : 15/952644
DATED : January 7, 2020
INVENTOR(S) : Chun-Mao Lin et al.

Page 1 of 2

It is certified that error appears in the above-identified patent and that said Letters Patent is hereby corrected as shown below:

In the Specification

Column 6, Lines 27-40:

"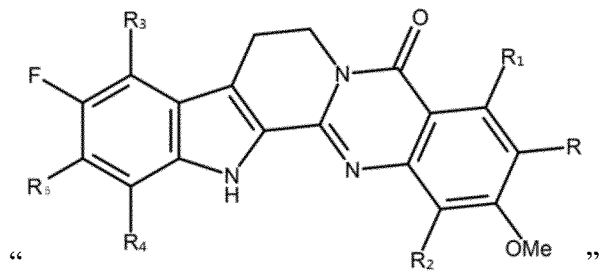"

Should read:

--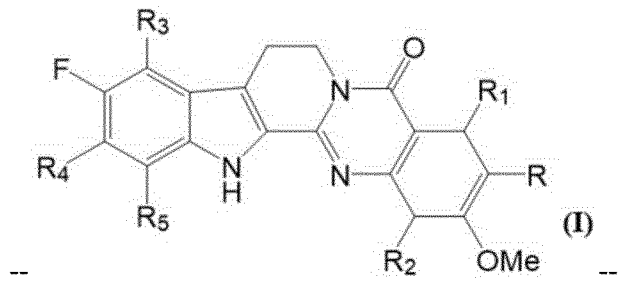--

Signed and Sealed this
Twentieth Day of December, 2022

Katherine Kelly Vidal
*Director of the United States Patent and Trademark Office*

CERTIFICATE OF CORRECTION (continued)
U.S. Pat. No. 10,526,333 B2

In the Claims

Column 17, Lines 10-22:

"
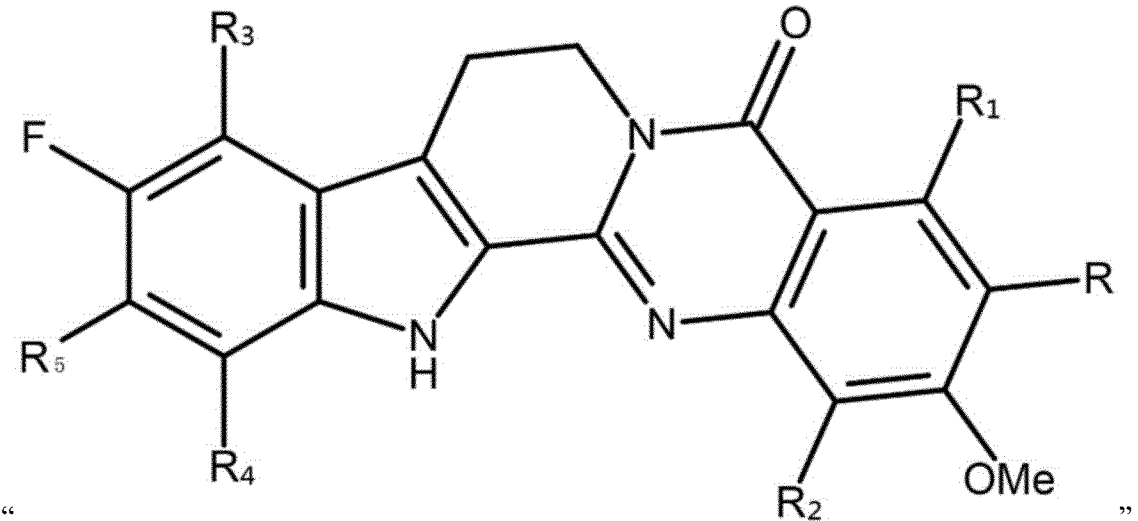
"

Should read:

--
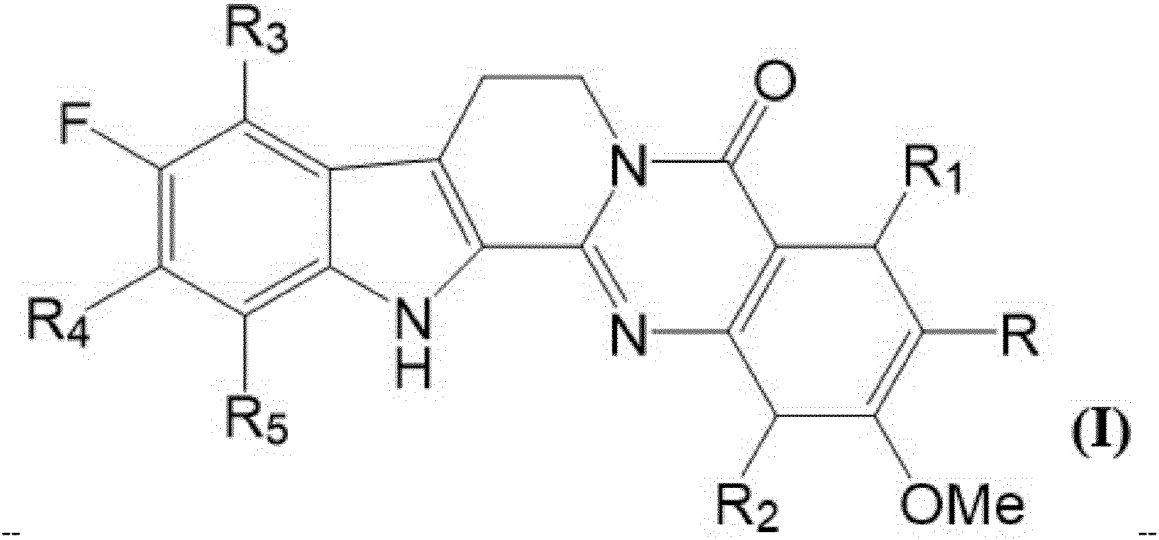
--